(12) United States Patent
Osypka et al.

(10) Patent No.: US 6,671,562 B2
(45) Date of Patent: Dec. 30, 2003

(54) HIGH IMPEDANCE DRUG ELUTING CARDIAC LEAD

(75) Inventors: Thomas P. Osypka, Palm Harbor, FL (US); Ronald van den Nieuwenhof, Odessa, FL (US)

(73) Assignee: Oscor Inc., Palm Harbor, FL (US)

( * ) Notice: Subject to any disclaimer, the term of this patent is extended or adjusted under 35 U.S.C. 154(b) by 0 days.

(21) Appl. No.: 10/281,744

(22) Filed: Oct. 28, 2002

(65) Prior Publication Data

US 2003/0093138 A1 May 15, 2003

Related U.S. Application Data

(60) Provisional application No. 60/344,984, filed on Nov. 9, 2001.

(51) Int. Cl.[7] .................................................. A61N 1/00
(52) U.S. Cl. ........................................ 607/120; 607/126
(58) Field of Search ................................ 607/120–123, 607/126–128; 600/374–381

(56) References Cited

U.S. PATENT DOCUMENTS

| | | |
|---|---|---|
| 3,545,439 A | 12/1970 | Duncan |
| 3,572,344 A | 3/1971 | Bolduc |
| 3,788,329 A | 1/1974 | Friedman |
| 3,804,098 A | 4/1974 | Friedman |
| 3,857,934 A | 12/1974 | Bernstein et al. |
| 4,018,220 A | 4/1977 | Emmett |
| 4,156,429 A | 5/1979 | Amundson |
| 4,191,741 A | 3/1980 | Hudson et al. |
| 4,220,153 A | 9/1980 | Dresback |
| 4,328,812 A | 5/1982 | Ufford et al. |
| 4,352,360 A | 10/1982 | King |
| 4,506,680 A | 3/1985 | Stokes |
| 4,538,623 A | 9/1985 | Proctor et al. |
| 4,577,642 A | 3/1986 | Stokes |
| 4,581,028 A | 4/1986 | Fox, Jr. et al. |
| 4,592,372 A | 6/1986 | Beranek |
| 4,596,576 A | 6/1986 | de Nijs |
| 4,601,893 A | 7/1986 | Cardinal |
| 4,606,118 A | 8/1986 | Cannon et al. |
| 4,711,251 A | 12/1987 | Stokes |
| 4,784,161 A | 11/1988 | Skalsky et al. |
| 4,819,661 A | 4/1989 | Heil, Jr. et al. |
| 4,819,662 A | 4/1989 | Heil, Jr. et al. |
| 4,844,099 A | 7/1989 | Skalsky et al. |
| 4,876,109 A | 10/1989 | Mayer et al. |
| 4,953,564 A | 9/1990 | Berthelsen |
| 4,961,931 A | 10/1990 | Wong |
| 4,972,848 A | 11/1990 | Di Domenico et al. |

(List continued on next page.)

FOREIGN PATENT DOCUMENTS

| | | |
|---|---|---|
| EP | 0 916 363 A2 | 5/1999 |
| WO | WO 91/19533 | 12/1991 |
| WO | WO 95/03083 | 2/1995 |
| WO | WO 96/08286 | 3/1996 |
| WO | WO 00/30610 | 6/2000 |

OTHER PUBLICATIONS

International Search Report dated Jun. 6, 2003.
*Pacing and Clinical Electrophysiology*, CARDIOSTIM '94 Proceedings, Edited by Rodolphe Ruffy and Jacques Mugica, Future Publishing Company, Inc., Armonk, New York, Nov. 1994, vol. 17, No. 11, Part II, pp. 1837–2227.

*Primary Examiner*—Mark Bockelman
(74) *Attorney, Agent, or Firm*—Scott D. Wofsy; Edwards & Angell, LLP

(57) ABSTRACT

A high impedance bipolar cardiac lead is disclosed that includes a lead body with a distal electrode assembly that includes an anodic ring electrode and a coaxially disposed cathodic tip electrode, wherein the anodic ring electrode and the cathodic tip electrode are separated from one another by a drug eluting insulating member.

24 Claims, 2 Drawing Sheets

U.S. PATENT DOCUMENTS

| | | | |
|---|---|---|---|
| 5,002,067 A | 3/1991 | Berthelsen et al. | |
| 5,003,992 A | 4/1991 | Holleman et al. | |
| 5,217,028 A | 6/1993 | Dutcher et al. | |
| 5,232,444 A | 8/1993 | Just et al. | |
| 5,254,121 A * | 10/1993 | Manevitz et al. | 606/128 |
| 5,255,693 A | 10/1993 | Dutcher et al. | |
| 5,269,770 A | 12/1993 | Conway et al. | |
| 5,282,844 A * | 2/1994 | Stokes et al. | 607/120 |
| 5,324,325 A | 6/1994 | Moaddeb | |
| 5,354,327 A | 10/1994 | Smits | |
| 5,408,744 A | 4/1995 | Gates | |
| 5,447,533 A | 9/1995 | Vachon et al. | |
| 5,489,294 A | 2/1996 | McVenes et al. | |
| 5,496,360 A | 3/1996 | Hoffmann et al. | |
| 5,522,874 A | 6/1996 | Gates | |
| 5,531,780 A | 7/1996 | Vachon | |
| 5,545,201 A * | 8/1996 | Helland et al. | 607/127 |
| 5,776,178 A | 7/1998 | Pohndorf et al. | |
| 5,833,715 A | 11/1998 | Vachon et al. | |
| 5,844,017 A | 12/1998 | Jamiolkowski et al. | |
| 5,871,529 A * | 2/1999 | Bartig et al. | 607/122 |
| 5,893,884 A | 4/1999 | Tu | |
| 5,902,330 A | 5/1999 | Ollivier et al. | |
| 5,987,746 A | 11/1999 | Williams | |
| 5,989,581 A | 11/1999 | Groenewegen | |
| 6,001,095 A * | 12/1999 | de la Rama et al. | 606/41 |
| 6,038,482 A | 3/2000 | Vachon | |
| 6,086,582 A | 7/2000 | Altman et al. | |
| 6,102,887 A | 8/2000 | Altman | |
| 6,134,463 A | 10/2000 | Wittkampf et al. | |
| 6,141,593 A | 10/2000 | Patag | |
| 6,181,972 B1 | 1/2001 | Guedeney et al. | |
| 6,198,973 B1 | 3/2001 | Doan et al. | |
| 6,298,272 B1 | 10/2001 | Peterfeso et al. | |
| 6,361,780 B1 | 3/2002 | Ley et al. | |
| 6,363,286 B1 | 3/2002 | Zhu et al. | |
| 6,405,091 B1 * | 6/2002 | Vachon et al. | 607/120 |

* cited by examiner

HIGH IMPEDANCE DRUG ELUTING CARDIAC LEAD

CROSS-REFERENCE TO RELATED APPLICATIONS

The subject application claims the benefit of priority to U.S. Provisional Patent Application Serial No. 60/344,984 filed Nov. 9, 2001, the disclosure of which is herein incorporated by reference in its entirety.

BACKGROUND OF THE INVENTION

1. Field of the Invention

The subject invention is directed to cardiac leads, and more particularly, to a high impedance drug eluting bipolar cardiac pacing lead.

2. Background of the Related Art

Implantable cardiac stimulation leads, including endocardial leads, are well known in the art. In general, these devices have an elongated flexible body with an electrode at one end for contacting cardiac tissue and a connector at the other end for mating with an automated stimulation device, namely a pacemaker. The electrode of an endocardial lead may be secured within a chamber of the heart by passive fixation through the use of a plurality of flexible tines which project outwardly from the end of the lead body, or by active fixation through the use of a helical fixation screw.

When an endocardial lead has been implanted in the heart, either by active or passive fixation, it has been determined that the cardiac tissue at the site of implantation will react favorably to the lead in the presence of a therapeutic drug, such as, for example, a steroid. Consequently, cardiac leads have been designed with means for delivering a therapeutic drug to the cardiac tissue at the implantation site.

One such example of a lead having drug delivery means is disclosed in U.S. Pat. No. 5,902,330 to Ollivier et al. which describes a pacing lead having a frusto-conical diffusion ring fixed in place by gluing. The diffusion ring is constructed of porous silicone and loaded with an active material, such as a steroid, for distributing the steroid in the region of the myocardium adjacent the electrode. Another example of a drug delivery device is disclosed in U.S. Pat. No. 6,361,780 to Ley et al. which describes a microporous bio-compatible collar or annulus having a therapeutic drug within its pores. The collar or annulus is preferably formed from a ceramic material and is designed to surround a portion of a lead or catheter.

In cardiac stimulation leads, it is advantageous to employ a high impedance electrode at the point of contact with the cardiac tissue. This provides more efficient stimulation of the heart tissue with lower current drain from the power source. This reduction in energy utilization, results in extending the battery life of the pacemaker.

One way to achieve high impedance is to increase the resistance of the conductors. However, this wastes energy. Another way to achieve high impedance is to minimize the geometric surface area of the stimulation electrode. Such an approach is disclosed, for example, in U.S. Pat. No. 5,282,844 to Stokes et al., the disclosure of which is herein incorporated by reference in its entirety Unfortunately, as the surface area of the pacing electrode decreases, it is more likely to cause trauma by penetrating into the cardiac tissue. Consequently, there are limitations as to size of the electrode.

It would be beneficial to provide a high impedance cardiac lead that overcomes the deficiencies of the prior art. More particularly, it would be beneficial to provide a high impedance cardiac lead that has a relatively small atraumatic pacing surface.

SUMMARY OF THE INVENTION

The subject invention is directed to a new and useful high impedance, bipolar cardiac lead. The lead includes an elongated flexible body formed from a bio-compatible insulative material and having opposed proximal and distal ends. An anodic ring electrode is operatively associated with the distal end of the lead body, and a cathodic tip electrode is coaxially disposed within the ring electrode so as to form an annular gap therebetween. An insulating member is disposed within the annular gap between the tip electrode and the ring electrode. A conventional lead connector is operatively associated with the proximal end of the lead body and is electrically connected to the ring and tip electrodes. Conductor means extend through the lead body to deliver energy from the connector to the ring and tip electrodes to stimulate cardiac tissue.

Preferably, the cathodic tip electrode has an exposed surface with an atraumatic convex configuration that essentially takes the form of a segment of a sphere. To achieve the requisite high impedance, the atraumatic cathodic tip electrode has an exposed surface area in the range of about between 0.50 mm$^2$ and 0.70 mm$^2$. In accordance with a preferred embodiment of the subject invention, the insulating member disposed between the anodic ring electrode and the cathodic tip electrode is adapted to elute an anti-inflammatory drug once implanted in a chamber of the heart. Preferably, the insulating member is formed from a compound that includes silicone rubber and a steroid.

The lead is preferably adapted for passive fixation and thus includes a plurality of flexible tines associated with a distal end portion of the lead body. It is envisioned however, that the lead of the subject invention may include an active fixation screw. The conductor means preferably includes a multifilar conductor coil having a number of filaments associated with the ring electrode and a number of filaments associated with the tip electrode, and the connector is preferably defined by a bipolar IS-1 type connector.

These and other aspects of the high impedance, drug eluting, bipolar cardiac lead of the subject invention will become more readily apparent to those having ordinary skill in the art from the following detailed description of the invention taken in conjunction with the drawings described hereinbelow.

BREIF DESCRIPTION OF THE DRAWINGS

So that those having ordinary skill in the art to which the subject invention pertains will more readily understand how to make and use the high impedance drug eluting cardiac lead of the subject invention, embodiments thereof will be described in detail hereinbelow with reference to the drawings, wherein.

DETAILED DESCRIPTION OF THE PREFERRED EMBODIMENTS

Figure 1:
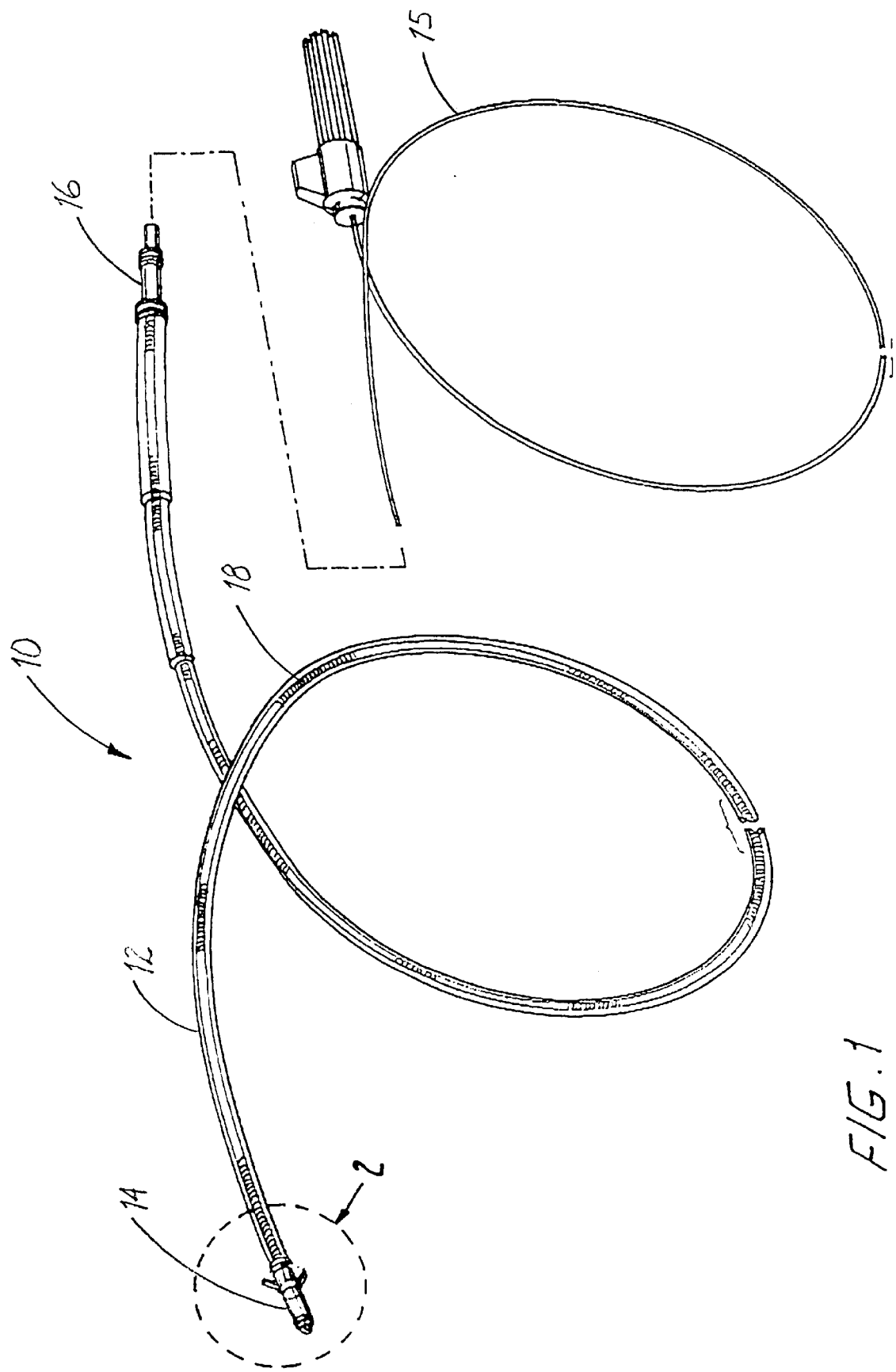
FIG. 1 is a perspective view of a high impedance drug eluting cardiac lead constructed in accordance with a preferred embodiment of the subject invention.

Referring now to the drawings wherein like reference numerals identify similar aspects of the cardiac lead of the subject invention, there is illustrated in FIG. 1 a bipolar, high impedance, drug eluting, passive fixation cardiac lead constructed in accordance with a preferred embodiment the subject invention and designated generally by reference numeral 10. Cardiac lead 10 includes an elongated flexible lead body 12 having opposed proximal and distal ends. The lead body 12 is formed from a bio-compatible insulative material such as silicone rubber, polyurethane or the like. Preferably, the lead body has an interior lumen for accommodating a relatively thin, rigid stylet 15 that confers rigidity to the normally flexible lead body during venous introduction.

With continuing reference to FIG. 1, a bipolar electrode assembly 14 is operatively associated with the distal end portion of the elongated lead body 12 for stimulating cardiac tissue. A connector 16 is operatively associated with the proximal end of the elongated lead body 12 for communicating with a corresponding adapter associated with a pulse generator or pacemaker (not shown). The connector 16 may be of any standard type, size or configuration such as, for example, a bipolar IS-1 type connector (International Standard ISO 5841.3:1992).

Figure 3:
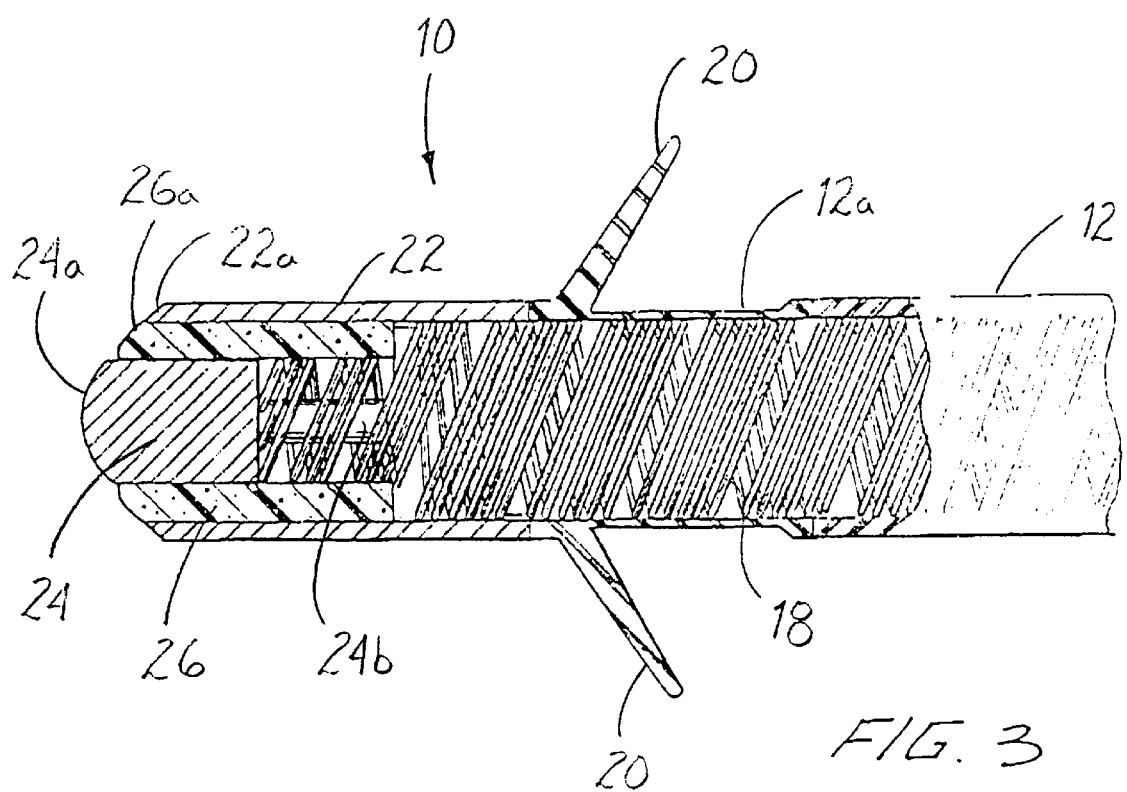
FIG. 3 is a side elevational view in cross-section of the distal end portion of the high impedance drug eluting cardiac lead of FIG. 1.

Connector 16 is electrically connected to the electrode assembly 14 by way of a conductor coil 18 that extends through the interior lumen of lead body 12. Preferably, conductor coil 18 is generally helical in configuration and includes one or more conductive wires or filaments. For example, the conductor coil 18 may be a multifilar conductor coil with as many as eight (8) filaments. Other conductors may be employed such as flexible low-ohm DFT drawn filled rope tubing. As illustrated in FIG. 3, for example, conductor coil 18 has six (6) elements or filaments. The structure and function of conductor coil 18 and its elements will be discussed in greater detail hereinbelow with reference to FIG. 3, as will alternative conductor configurations.

Figure 2:
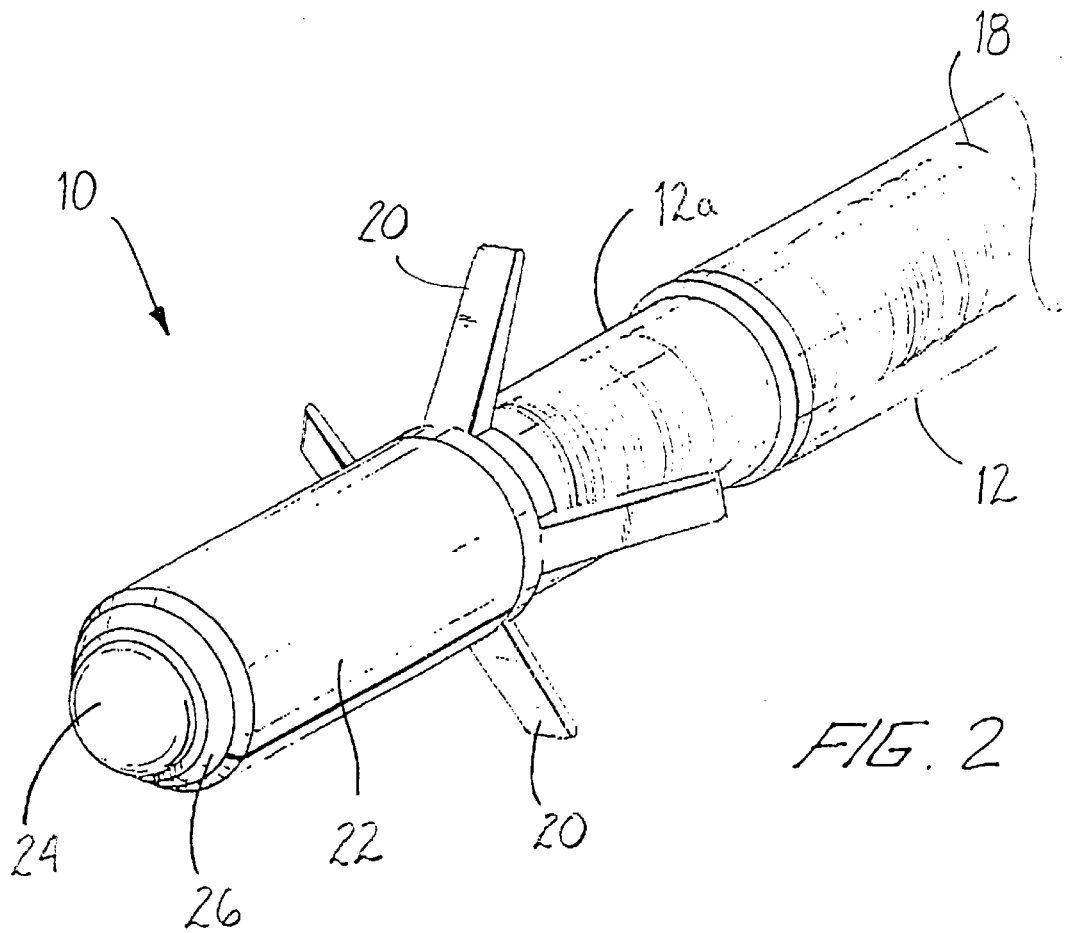
FIG. 2 is an enlarged perspective view in cross-section of the distal end portion of the high impedance drug eluting cardiac lead of FIG. 1.

The cardiac lead 10 illustrated in FIGS. 1 through 3, is adapted and configured for passive fixation within the heart. Therefore, the distal end portion of lead body 12 is provided with a plurality of flexible tines 20 that are formed from silicone rubber or a like material which are adapted to keep the lead tip securely anchored within the trabeculae of the heart. A section of the lead body designated by reference numeral 12a located proximal to the flexible tines 20 has a reduced diameter to accommodate the flexible tines in a retracted orientation when the lead body passes through a cannula or introducer sheath. In embodiments of the subject invention in which the distal end portion of lead body 12 is generally straight, as illustrated in FIGS. 2 and 3, the flexible tines 20 are used to anchor the lead within the right ventricle. In other embodiments of the subject invention where the distal end portion of lead body 12 has a preformed J-shaped configuration, the flexible tines would anchor the lead in the right atrium. It is also envisioned that the cardiac lead of the subject invention could be configured with an active fixation screw, as is well known in the art. The fixation screw may be extendable/retractable and manipulated by way of a screw driver stylet or similar mechanism.

Referring to FIGS. 2 and 3, electrode assembly 14 is adapted and configured to provide a high impedance pacing surface for stimulating cardiac tissue. Electrode assembly 14 includes a radially outer anodic ring electrode 22 and a radially inner, preferably solid, cathodic tip electrode 24 which are arranged coaxially with respect to one another. More particularly, an annular gap is formed between the inner periphery of the anodic ring electrode 22 and the outer periphery of the cathodic tip electrode 24. An elastomeric insulating tube 26 is firmly disposed within the gap between the ring electrode 22 and the tip electrode 24 for electrically isolating one electrode from the other from the other. It is envisioned that in an embodiment of the subject invention the radially inner tip electrode could serve as an anode with the radially outer ring electrode serving as the cathode.

The outer ring electrode 22 is preferably about thrice the axial length of the insulating inner tip electrode 24, and the insulating tube 26 is about twice the axial length of the central tip electrode 24. In one embodiment of the subject invention, the outer ring electrode is about 3 mm in length, the insulating tube 26 is about 2 mm in length, and the tip electrode is about 1 mm in length. As best seen in FIG. 2, ring electrode 22 and insulating tube 26 have coincident tapered leading edges 22a, 26a, respectively, while the tip electrode 24 has a generally convex leading surface 24a. Together, these three geometric features form an atraumatic pacing surface for the lead.

Preferably, the two electrodes 22, 24 are coated with or formed from platinum, stainless steel MP35N, a platinum-iridium alloy or a similar material bio-compatible metallic material. The insulating tube 26 is preferably formed from an elastomer, such as polyurethane, silicone rubber or a similar material. In one embodiment of the subject preferably, insulating tube 26 serves as a drug elution device. Thus, it is formed from a compound that includes an elastomeric material and a therapeutic drug. In use, the drug elutes from the elastomer over time, having a desirable effect on surrounding cardiac tissue. Suitable drugs include anti-inflammatory drugs such as steroids, including for example, dexamethasone sodium phosphate and dexamethasone sodium acetate. Such steroids control inflammation in the tissue located at the implantation site of the lead. Other steroids and non-steroidal based drugs may also be used. In an embodiment of the subject invention, the drug eluting insulating tube 26 includes about 15% to 25% by weight anti-inflammatory drug.

In an embodiment of the subject invention, insulating tube 26 is formed by mixing liquid silicone rubber (LSR) together with the steroid. The composition is then extruded into a tubular form and subsequently cut into rings having a desired length and a durometer of about 65 to 90 Shore A. Alternatively, the composition may be used to mold tubes of a desired length. In either instance, after formation, the tubes are glued in place using a silicone adhesive.

With continuing reference to FIGS. 2 and 3, plural elements or filaments of the multifilar conductor coil 18 are operatively connected to the inner periphery of the radially outer ring electrode 22 of electrode assembly 14. Other filaments or elements of the multifilar conductor coil 18 are operatively connected to the proximal end of the radially inner tip electrode 24 of electrode assembly 14. For example, as shown, three (3) filaments may be associated with the outer ring electrode 22, and three (3) filaments may be associated with the inner ring electrode 24. It is envisioned that one or more of the filaments associated in the multifilar coil may be inactive and serve to insulate the active filaments from one another.

The three filaments associated with the radially outer ring electrode 22 may be welded or secured in a similar manner. The three filaments associated with the radially inner tip electrode 24 may be welded to the proximal end surface of the electrode or crimped to the proximal appendage 24b thereof. Those skilled in the art will readily appreciate that by providing multiple electrical connections between the proximal connector 16 and each of the distal electrodes 22, 24, there is redundancy built into the lead if a filament has a short or otherwise becomes disabled during use.

It is envisioned that the conductor coil extending through the lead body 12 from the proximal connector 16 to the distal electrode assembly 14 may take the form of a coaxial conductor coil having an inner conductor coil operatively connected to the radially inner cathodic tip electrode, and an outer conductor coil operatively connected to the radially outer anodic ring electrode, wherein the inner and outer conductor coils are insulated from one another.

The bipolar electrode assembly 14 of the subject invention is adapted and configured to provide a relatively high impedance. This achieved by minimizing the surface area of the cathode tip electrode 24. For example, in a preferred embodiment of the subject invention, the convex cathodic tip electrode 24 has an exposed pacing surface which takes the form of a segment of a sphere with a radius of about 0.50 mm and a radial height of about 0.20 mm. In such an instance, the area of the exposed pacing surface of the cathodic tip electrode 24 is about approximately 0.62 mm$^2$. This small exposed pacing surface area results in higher current densities during stimulation, thereby providing more efficient stimulation of the heart with lower current drain on the pacemaker battery. Preferably, where the overall diameter of lead body 12 is about 2.0 mm, the exposed pacing surface area of the cathodic tip electrode 24 is in the range of about between 0.50 mm$^2$ and 0.70 mm$^2$.

Although the high impedance, drug eluting, bipolar cardiac lead of the subject invention have been described with respect to preferred embodiments, those skilled in the art will readily appreciate that changes and modifications may be made thereto without departing from the spirit and scope of the subject invention as defined by the appended claims.

What is claimed is:

1. A high impedance bipolar cardiac lead comprising:
   a) an elongated lead body having opposed proximal and distal ends;
   b) a ring electrode operatively associated with the distal end of the lead body and defining an inner peripheral surface;
   c) a tip electrode coaxially disposed within the ring electrode and defining an (outer peripheral surface such that an annular gap is formed between the inner peripheral surface of the ring electrode and the outer peripheral surface of the tip electrode;
   d) a drug eluting insulating member disposed within the annular gap formed between the outer peripheral surface of the tip electrode and the inner peripheral surface of the ring electrode;
   e) a connector operatively associated with the proximal end of the lead body and electrically connected to the ring and tip electrodes; and
   f) conductor means extending through the lead body for delivering energy from the connector to the ring and tip electrodes to stimulate cardiac tissue.

2. A high impedance bipolar cardiac lead as recited in claim 1, wherein the ring electrode serves as an anode and the tip electrode serves as a cathode.

3. A high impedance bipolar cardiac lead as recited in claim 2, wherein the cathodic tip electrode has an exposed surface with a convex configuration.

4. A high impedance bipolar cardiac lead as recited in claim 3, wherein the cathodic tip electrode has an exposed surface area in the range of about between 0.50 mm$^2$ and 0.70 mm$^2$.

5. A high impedance bipolar cardiac lead as recited in claim 3, wherein the axial length of the ring electrode is about thrice the axial length of the tip electrode, and the axial length of the insulating member is about twice the axial length of the tip electrode.

6. A high impedance bipolar cardiac lead as recited in claim 1, wherein the insulating member is formed from a compound comprising an elastomer and a medicament.

7. A high impedance bipolar cardiac lead as recited in claim 6, wherein the compound from which the drug eluting insulating member is formed includes silicone and a steroid.

8. A high impedance bipolar cardiac lead as recited in claim 7, wherein the steroid forms about 15% to 20% of the weight of the compound from which the insulating member is formed.

9. A high impedance bipolar cardiac lead as recited in claim 1, wherein the lead is adapted for passive fixation and includes a plurality of flexible tines associated with a distal end portion of the lead body.

10. A high impedance bipolar cardiac lead as recited in claim 1, wherein the conductor means includes a multifilar conductor coil having a number of filaments associated with the ring electrode and a number of filaments associated with the tip electrode.

11. A high impedance bipolar cardiac lead as recited in claim 1, wherein the connector is defined by a bipolar IS-1 type connector.

12. A high impedance bipolar cardiac lead, comprising:
   a) an elongated lead body having opposed proximal and distal ends;
   b) an anodic ring electrode operatively associated with the distal end of the lead body and defining an inner peripheral surface;
   c) a cathodic tip electrode coaxially disposed within the ring electrode and defining an outer peripheral surface such that an annular gap is formed between the inner peripheral surface of the ring electrode and the outer peripheral surface of the tip electrode;
   d) a drug eluting insulating member disposed within the annular gap formed between the outer peripheral surface of the cathodic tip electrode and the inner peripheral surface of the anodic ring electrode;
   e) a connector operatively associated with the proximal end of the lead body and electrically connected to the ring and tip electrodes; and
   f) conductor means extending through the lead to deliver electrical energy from the connector to the ring and tip electrodes to stimulate cardiac tissue.

13. A high impedance bipolar cardiac lead as recited in claim 12, wherein the cathodic tip electrode has an exposed surface with a convex configuration.

14. A high impedance bipolar cardiac lead as recited in claim 13, wherein the cathodic tip electrode has an exposed surface area in the range of about between 0.50 mm$^2$ and 0.70 mm$^2$.

15. A high impedance bipolar cardiac lead as recited in claim 12, wherein the drug eluting insulating member is formed from a compound comprising an elastomer and an anti-inflammatory drug.

16. A high impedance bipolar cardiac lead as recited in claim 15, wherein the compound from which the insulating member is formed includes silicone and a steroid.

17. A high impedance bipolar cardiac lead as recited in claim 16, wherein the steroid forms about 15% to 20% of the weight of the compound from which the insulating member is formed.

18. A high impedance bipolar cardiac lead as recited in claim 12, wherein the lead is adapted for passive fixation and includes a plurality of flexible tines associated with a distal end portion of the lead body.

19. A high impedance bipolar cardiac lead as recited in claim 12, wherein the conductor means includes a multifilar conductor coil having a number of filaments associated with the anodic ring electrode and a number of filaments associated with the cathodic tip electrode.

20. A high impedance bipolar cardiac lead as recited in claim 12, wherein the connector is defined by a bipolar IS-1 type connector.

21. A high impedance bipolar cardiac lead as recited in claim 12, wherein the axial length of the ring electrode is about thrice the axial length of the tip electrode, and the axial length of the insulating member is about twice the axial length of the tip electrode.

22. A high impedance bipolar cardiac lead, comprising:
   a) a lead body having opposed proximal and distal ends; and
   b) an electrode assembly operatively associated with the distal end of the lead body and including an anodic ring electrode defining a leading edge and a coaxially disposed cathodic tip electrode defining a leading surface, wherein the anodic ring electrode and the cathodic tip electrode are separated from one another by a drug eluting insulating member having a leading edge, and wherein the leading edges of the ring electrode and insulating member are coincident, and cooperate with the leading surface of the tip electrode to form an atraumatic pacing surface for the lead.

23. A high impedance bipolar cardiac lead as recited in claim 22, further comprising a connector operatively associated with the proximal end of the lead body and electrically connected to the ring and tip electrodes.

24. A high impedance bipolar cardiac lead as recited in claim 23, further comprising a multifilar conductor coil extending through the lead body to deliver electrical energy from the connector to the ring and tip electrodes to stimulate cardiac tissue.

* * * * *